(12) United States Patent
Ramakrishnan (10) Patent No.: US 7,221,158 B1
(45) Date of Patent: May 22, 2007

(54) PERMEABILITY DETERMINATIONS FROM NUCLEAR MAGNETIC RESONANCE MEASUREMENTS

(75) Inventor: Terizhandur S. Ramakrishnan, Bethel, CT (US)

(73) Assignee: Schlumberger Technology Corporation, Ridgefield, CT (US)

( * ) Notice: Subject to any disclaimer, the term of this patent is extended or adjusted under 35 U.S.C. 154(b) by 0 days.

(21) Appl. No.: 11/299,985

(22) Filed: Dec. 12, 2005

(51) Int. Cl.
*G01V 3/00* (2006.01)

(52) U.S. Cl. .................... 324/303; 324/300

(58) Field of Classification Search .............. 324/303, 324/300, 309, 307, 316, 318; 73/152.05
See application file for complete search history.

(56) References Cited

U.S. PATENT DOCUMENTS

| | | | |
|---|---|---|---|
| 2,747,401 A | | 5/1956 | Doll |
| 4,933,638 A | | 6/1990 | Kenyon et al. |
| 5,023,551 A | | 6/1991 | Kleinberg et al. |
| 5,156,205 A | * | 10/1992 | Prasad .................. 166/250.02 |
| 5,363,041 A | | 11/1994 | Sezginer |
| 5,486,761 A | | 1/1996 | Sezginer |
| 5,680,043 A | * | 10/1997 | Hurlimann et al. ......... 324/303 |
| 6,047,595 A | * | 4/2000 | Herron et al. ............ 73/152.05 |
| 6,369,567 B1 | * | 4/2002 | Song et al. .................. 324/303 |
| 6,690,166 B2 | * | 2/2004 | Ni et al. ...................... 324/309 |
| 6,703,832 B2 | * | 3/2004 | Heaton et al. .............. 324/303 |

OTHER PUBLICATIONS

Timur et al., "Pulsed Nuclear Magnetic Resonance Studies of Porosity, Movable Fluid, and Permeability of Sandstones", Journal of Petroleum Technology, (Jun. 1969, pp. 775-786).
Goode, P. et al., "Influence of an Invaded Zone on a Multiprobe Formation Tester", SPE Formation Evaluation, Mar. 1996, pp. 31-40.
Mohaghegh et al., "Permeability Determination from Well Log Data", SPE Formation Evaluation, Sep. 1997. pp. 170-174.
Ambegaokar et al., "Hopping Conductivity in Disordered Systems", Physical Review B, vol. 4, No. 8, Oct. 15, 1971, pp. 2612-2620.
Banavar et al., "Characteristic Pore Sizes and Transport in Porous Media", Physical Review B, vol. 35, No. 13, May 1, 1987, pp. 7283-7286.
Johnson et al., "New Pore-Size Parameter Characterizing Transport in Porous Media", Physical Review Letters, vol. 57, No. 20, Nov. 17, 1986, pp. 2564-2567.
Kenyon et al., "A Three-Part Study of NMR Longitudinal Relaxation Properties of Water-Saturated Sandstones", SPE Formation Evaluation, Sep. 1988, pp. 622-636.
Larson et al., "Effects of Sample Size on Capillary Pressures in Porous Media", Powder Technology, 30 (1981), pp. 123-128.
MacMullin et al., "Characteristics of Porous Beds and Structures", vol. 2, No. 3, A. I. Ch. E. Journal, pp. 393-402.

(Continued)

*Primary Examiner*—Brij B. Shrivastav
(74) *Attorney, Agent, or Firm*—David P. Gordon; Vincent Loccisano; Jody Lynn DeStefanis (57) ABSTRACT

Permeability determinations are made from NMR measurements of a logging tool. The NMR measurements are used to find an observed critical spin—spin relaxation time which is used in conjunction with an in situ determination of surface relaxivity of a rock in order to generate permeability determinations.

45 Claims, 4 Drawing Sheets

OTHER PUBLICATIONS

Ramakrishnan et al., "Effect of Capillary Number on the Relative Permeability Function for Two Phase Flow in Porous Media", Powder Technology, 48 (1986) 99-124.

Ramakrishnan et al., "Two-Phase Distribution on Porous Media: An application of Percolation Theory", Int. J. Multiphase Flow, vol. 12, No. 3, pp. 357-388, 1986.

Ramakrishnan et al., "A Petrophysical and Petrographic study of Carbonate Cores from the Thamama formation", SPE 49502, 1998.

Shante et al., "An Introduction to Percolation Theory", Advances Phys. 20, No. 85, May 1971, pp. 325-357.

Wilkinson et al., "Invasion percolation: a new form of percolation theory", J. Phys. A.: Math. Gen. 16 (1983) pp. 3365-3376.

Slichter et al., "Advanced Concepts in Pulsed Magnetic Resonance", Springer Series in Solid-State Sciences, Principles of Magnetic Resonance, Chapter 8, pp. 367-371.

Seevers, "A Nuclear Magnetic Method for Determining the Permeability of Sandstones", Transactions of the SPWLA Seventh Annual Logging Symposium, May 9-11, 1966.

Freedman, "Advances in NMR Logging", JPT, Jan. 2006, pp. 60-66.

Kenyon et al., "Nuclear Magnetic Resonance Imaging-Technology for the 21st Century", Oilfield Review, Autumn 1995, pp. 19-33.

* cited by examiner

PERMEABILITY DETERMINATIONS FROM NUCLEAR MAGNETIC RESONANCE MEASUREMENTS

BACKGROUND OF THE INVENTION

1. Field of the Invention

This invention relates broadly to methods for investigating subsurface earth formations. More particularly, this invention relates to methods of determining the permeability of an earth formation utilizing information obtained from a nuclear magnetic resonance (NMR) tool.

2. State of the Art

The determination of permeability and other hydraulic properties of formations surrounding boreholes is very useful in gauging the producibility of formations, and in obtaining an overall understanding of the structure of the formations. For the reservoir engineer, permeability is generally considered a fundamental reservoir property, the determination of which is at least equal in importance with the determination of porosity, fluid saturations, and formation pressure. When obtainable, cores of the formation provide important data concerning permeability. However, cores are difficult and expensive to obtain, and core analysis is time consuming and provides information about very small sample volumes. In addition, cores, when brought to the surface, may not adequately represent downhole conditions. Thus, in situ determinations of permeability that can quickly provide determinations of permeabilities over large portions of the formation are highly desirable.

Suggestions regarding in situ determination of permeability via the injection or withdrawal of fluid into or from the formation and the measurement of pressures resulting therefrom date back at least to U.S. Pat. No. 2,747,401 to Doll (1956). The primary technique presently used for in situ determination of permeability is the "drawdown" method where a probe of a formation testing tool is placed against the borehole wall, and the pressure inside the tool is brought below the pressure of the formation, thereby inducing fluids to flow into the formation testing tool. By measuring pressures and/or fluid flow rates at and/or away from the probe, and processing those measurements, determinations regarding permeability are obtained. Currently, such determinations are being made via the MDT (a trademark of Schlumberger) tool or Modulation Formation Dynamics Tester, which is a commercially successful tool of Schlumberger, the assignee hereof. However, one drawback to the drawdown method is that it is time consuming and therefore the number of locations at which sampling is accomplished is necessarily quite limited.

Starting in the 1960's it was proposed to use nuclear magnetic resonance (NMR) measurements to measure formation permeability. In particular, it is well known that the strength of a NMR signal is directly proportional to the number of resonated spins present in a probed volume. Because hydrogen is the nucleus of choice in most borehole measurements, and because NMR tools can be tuned in frequency to resonate a particular nuclear species, the signal amplitude of a tuned tool can be arranged to measure the number of hydrogen atoms in the formation. The number of hydrogen atoms in the formation in turn is related to fluid filled porosity. In addition to being sensitive to hydrogen density, NMR tools are sensitive to the environment of the hydrogen being probed. For example, hydrogen in a bound or "irreducible" fluid typically has a spin-lattice relaxation time (T1) in the milliseconds to tens of milliseconds, while free or producible fluid has a T1 in the range of tens to hundreds of milliseconds. Thus, in addition to correlating well to porosity, the measurements resulting from the NMR sequences applied to the formation provide information which may be correlated with the "free fluid index", permeability, and residual oil saturation. The concept of "free fluid index" is largely based on work by Seevers, "A Nuclear Magnetic Method for Determining the Permeability of Sandstones", $7^{th}$ SPWLA Logging Symp. (1966, Paper L), and Timur, "Pulsed Nuclear Magnetic Resonance Studies of Porosity, Movable Fluid, and Permeability of Sandstones", Journal of Petroleum Technology, (June 1969, pp. 775–786). Currently, NMR measurements in the borehole are being made via the CMR (a trademark of Schlumberger) or Combinable Magnetic Resonance tool, and the MRX (a trademark of Schlumberger) or Magnetic Resonance expert tool which features a gradient magnetic field and multiple frequencies of operation; both of which are commercially successful tools of Schlumberger, the assignee hereof. Details of NMR borehole tools may be seen with reference to U.S. Pat. No. 4,933,638 to Kenyon et al., U.S. Pat. No. 5,023,551 to Kleinberg et al., and U.S. Pat. No. 5,486,761 to Sezginer, all of which are hereby incorporated by reference herein in their entireties.

NMR tools function on the principle that the nuclei of elements such as hydrogen have an angular momentum ("spin") and a magnetic moment. The nuclear spins will align themselves along an externally applied static magnetic field which may be applied by the NMR tool. The equilibrium situation can be disturbed by a pulse of an oscillating magnetic field provided by the NMR tool which tips the spins away from the static field direction. After tipping, two things occur simultaneously. First, the spins precess around the static field at a particular frequency (i.e., the Larmor frequency), given by $\omega_o = \gamma B_o$ where $B_o$ is the strength of the static field and $\gamma$ is the gyromagnetic ratio, a nuclear constant. Second, the spins return to the equilibrium direction according to a decay time known as the "spin-lattice relaxation time" or T1. T1 is controlled totally by the molecular environment and is typically ten to one thousand milliseconds in rocks. Each spin can be thought of as moving back toward equilibrium in a very tight pitch spiral during the T1 decay.

Also associated with the spin of molecular nuclei is a second relaxation time known as the "spin—spin relaxation time" or T2. At the end of a ninety degree tipping pulse, all the spins are pointed in a common direction perpendicular to the static field, and they all precess at the Larmor frequency. However, because of small inhomogeneities in the static field due to imperfect instrumentation or microscopic material heterogeneities, each nuclear spin precesses at a slightly different rate. Hence, after a time long compared to the precession period, but shorter than T1, the spins will no longer be precessing in unison. When this dephasing is due to static field inhomogeneity of the apparatus, the dephasing is called T2*. When it is due to properties of the material, the dephasing time is called T2. For rocks, T2 is generally approximately one-half of T1.

While many different methods for measuring T1 have been developed, a relatively standard method known as the CPMG (Carr-Purcell-Meiboom-Gill) sequence has been used to measure T2. The CPMG sequence is a well-known sequence of pulses which cancel out the effect of the apparatus-induced inhomogeneities and permit a determination of dephasing due to material properties; i.e., a measurement of T2. Modifications to the CPMG sequence such as set forth in previously incorporated U.S. Pat. No. 5,023,551 to Kleinberg et al. have been utilized to improve thereupon.

As is well known in the art, after applying the CPMG sequences, NMR tools measure a voltage or magnetization over time which is designated M(t). As will be discussed hereinafter, M(t) is a function of porosity $\phi$, the observed T2 decay $T_{2o}$, and a probability density function $g_0$ of the distribution of T2 relaxation in the rock pores contributing to the signal. Thus, from M(t), the porosity $\phi$ can be calculated. Also, for water saturated pores, a correlation has been developed which permits a determination of permeability k according to $k=C_1\phi^2 T_{2lm}^2$, where $C_1$ is a constant, and $T_{2lm}$ is the T2 log mean.

While the permeability determination utilizing the correlation yields reasonable results for water saturated pores, it has been more difficult to measure permeability in rocks where there is water and oil. Where there is water and oil, if the water wets the pore walls, then the oil in the pore relaxes as if there is no pore wall. As a result, the $T_{2lm}$ appears to be larger than it should otherwise be, and the permeability determination is skewed.

One manner of correcting for the problem of measuring permeability in the presence of water and oil is to generate an indication of the T2 signal, and to partition the signal via a cutoff time (e.g., 33 milliseconds) with the T2 signal prior to the cutoff time being considered related to the bound water. The bound water is the irreducible water saturation ($s_{wi}$) which is related to permeability according to the Timur correlation $k=c\phi^b/s_{wi}^d$, where c is a constant usually taken as 0.136, b is a constant usually taken as 4.4, and d is a constant usually taken as 2. See SPE 30978 (1968).

The Timur correlation, while sometimes providing reasonable results, is considered error prone. Indeed, historically, the permeability predictors based on NMR relaxation have been hindered by a host of uncertainties, including (i) unknown surface relaxivity (i.e., rate at which magnetization decays at a pore wall) parameter, (ii) failure of correlations developed for fully saturated rocks when applied to hydrocarbon zones, and (iii) inadequate pore network physics in relating T2 distribution to permeability.

SUMMARY OF THE INVENTION

It is therefore an object of the invention to provide methods for generating accurate determinations of a formation permeability.

It is another object of the invention to utilize NMR tool determinations in order to provide enhanced permeability determinations in areas of lithology in which a fluid drawdown tool measurement has been made.

It is a further object of the invention to utilize an understanding of the physics of hydrocarbon trapping in making determinations of permeability.

It is an additional object of the invention to determine permeability of a formation in terms of a critical observed spin—spin relaxation time ($T_{2oc}$) which is calculable from an NMR tool.

Another object of the invention is to provide methods of accurately determining permeability in oil zones.

In accord with these objects, which will be discussed in detail below, methods for determining formation permeability utilizing an NMR tool are provided where the NMR tool is utilized to find a critical observed spin—spin relaxation time ($T_{2oc}$), and $T_{2oc}$ is utilized in determining the formation permeability. More particularly, according to the methods of the invention, a drawdown permeability determination is made at a first location using a borehole tool such as the MDT, and $T_{2oc}$ values generated by an NMR tool are utilized to generate permeability determinations for other locations of similar lithology (e.g., in the same stratum) as the first location. The generated permeability determinations may take the form of a continuous permeability log of the stratum, strata or lithology of interest.

In one embodiment of the invention where the MDT permeability determination is available in a water zone (i.e., as indicated by resistivity logs, or in the absence of which, if the fluid drawn into the MDT was entirely water), the $T_{2oc}$ value generated from measurements made by the NMR tool at the location of an MDT drawdown test is used in conjunction with the MDT drawdown permeability $k_{dd}$ to provide a value for the surface relaxivity $\rho$. The surface relaxivity is then used in conjunction with $T_{2oc}$ values generated from the NMR tool measurements at other locations of similar lithology to find the permeability k at those other locations of similar lithology.

In another embodiment of the invention where an oil zone is encountered and a multiprobe MDT is utilized to permit a determination of single phase permeability (e.g., a horizontal dual probe permeability $k_{hdp}$), the single phase permeability may be used in conjunction with the $T_{2oc}$ value generated from measurements made by the NMR tool at the MDT test location to provide a value for the surface relaxivity $\rho$. Again, the surface relaxivity may then be used in conjunction with $T_{2oc}$ values generated from the NMR tool measurements at other locations of similar lithology to find the permeability k at those other locations of similar lithology.

In a third embodiment of the invention where an oil zone is encountered and only single probe MDT data is available, a critical percolation probability for water-occupied pores is used together with other information and/or assumptions in order to permit a determination of the critical observed T2 for pores governing water mobility $T_{2woc}$. From $T_{2woc}$ and the effective permeability to water as determined from the single probe MDT, a continuous log of the effective permeability to water $k°_{ew}$ in the lithology stratum of interest can be generated. In addition, the $T_{2woc}$ value generated from measurements of the NMR tool at the location of an MDT drawdown test is used in conjunction with the MDT drawdown permeability to provide a value for the surface relaxivity p. The surface relaxivity is then used in conjunction with $T_{2oc}$ values generated from the NMR tool determinations at other locations of similar lithology to find the single phase permeability k at those other locations of similar lithology, even though two immiscible phases are present.

In a fourth embodiment of the invention, single phase permeability is determined by an NMR tool even in the absence of draw-down permeability data, provided a value for the surface relaxivity is known a priori for a region of interest. The fourth embodiment utilizes many of the aspects of the third embodiment.

Additional objects and advantages of the invention will become apparent to those skilled in the art upon reference to the detailed description taken in conjunction with the provided Figures.

DETAILED DESCRIPTION OF THE PREFERRED EMBODIMENTS

Before turning to the Figures it is useful to understand the theoretical underpinnings of the invention. On a very basic level it should be understood that a highest or first order term of the permeability may be defined by the most resistant pore in the least resistant path. Stated another way, in finding the "oil permeability" of a rock, it will be appreciated that the permeability from point A to point B in the rock is controlled by which of the connecting pathways through the rock has the largest pores (i.e., the least resistant path). The smallest (i.e., most resistant) pore in that pathway acts as a constriction to the pathway.

Those skilled in the art will also appreciate that where water has invaded a formation, because of surface tension physics, the water tends to occupy the smallest pores first in water-wet media.

Using this basic understanding of rock pores and permeability, the connection between magnetization decay and permeability may be understood. In particular, as practiced today, measurements of the transverse magnetization decay of protons precessing in a magnetic field is obtained by using a CPMG sequence or a modification thereof. The measurements are denoted M(t). In the usual paradigm of NMR interpretation it is assumed that (i) the pore space of the rock can be represented by a probability density function of pore sizes (or equivalently volume to surface areas of pores), (ii) magnetization diffusion between pores is strongly hindered by the intervening throats, and (iii) relaxation in each pore is surface relaxivity controlled. Mathematically, the last assumption means that l$\rho$lD<<1, where/is the volume to surface ratio of the pore, $\rho$ is the surface relaxivity, and D is the self-diffusion coefficient of water. The observed transverse relaxation time $T_{2o}$ associated with each pore is then $$\frac{1}{T_{2o}} = \frac{1}{T_{2b}} + \frac{\rho}{l} \tag{1}$$

where $T_{2b}$ is the bulk transverse relaxation of the fluid. The magnetization relaxation in each pore behaves as $\exp(-t/T_{2o})$.

It may be assumed that $\rho$ is a constant for a given rock. Since l/$\rho$ is an intrinsic relaxation time scale, the intrinsic relaxation time for the rock (excluding effects of liquid) $T_{2i}$ can be defined according to:

$$\frac{1}{T_{2i}} = \frac{\rho}{l} \tag{2}$$

The volume probability density function with respect to/denoted as $g_l(l)$ is $$\int_0^\infty g_l(l)dl = 1 \tag{3}$$

Similarly, $g_i(T_{2i})$ is the probability density function (pdf) with respect to $T_{2i}$. It follows then that $$\frac{1}{\rho}g_i(T_{2i}) = \frac{1}{\rho}g_i\left(\frac{l}{\rho}\right) = g_l(l) \tag{4}$$

With respect to the observed relaxation times, the pdf $g_o$ satisfies $$\int_0^\infty g_o(T_{2o})dT_{2o} = 1 \tag{5}$$

It should be noted that $g_o(T_{2o}) = 0 \ \forall T_{2o} > T_{2b}$. It can also be seen that $$g_l(l) = \rho\left(\frac{T_{2o}}{l}\right)^2 g_o(T_{2o}) \text{ with } T_{2o} = \frac{lT_{2b}}{l + \rho T_{2b}}. \tag{6}$$

The observed magnetization (i.e., the measurement made by the NMR tool) is a composite of contributions from all pores and is given by $$M(t) = \phi \int_0^\infty g_o(T_{2o})\exp(-t/T_{2o})dT_{2o} \tag{7}$$

The typical processing procedure is to use M(t) to calculate $g_o(T_{2o})$, an algorithm for which is provided by U.S. Pat. No. 5,363,041 to Sezginer. Presently, the $g_o$ distribution is used to compute a permeability measure. Little distinction is made between $T_{2i}$ and $T_{2o}$ because $T_{2b}$ is a few times larger than the observed $T_{2i}$ especially in medium to low permeability sandstones. Generally, however, one needs to at least translate $g_o$ to $g_l$ through Equation 6 before applying existing correlations such as those proposed by Kenyon, W. E. et al., "A Three-part Study of NMR Longitudinal Relaxation Studies of Water-Saturated Sandstones", *SPE Form. Eval.* 3, p 662–636 (1988), although this is not explicit in their correlation.

For transport properties, it is useful to deal with $n_l(l)$, the number probability density function which is derived according to $$n_l(l) = \frac{g_l(l)/V(l)}{\int_0^\infty \frac{g_l l}{V(l)}dl}, \tag{8}$$

where it is assumed that a single length scale parameter l determines the volume of a pore V. Given the number probability density function, the critical length scale that is important for computing permeability can be estimated. The critical length scale, denoted $l_c$ will be the most resistant connection in the least resistant pathway, and is given by the smallest pore size within the set of largest pore sizes constituting the fraction equal to critical percolation probability $p_c$. Although not stated explicitly, this connection was first used in Macmullin, R. B. et al., "Characteristics of Porous Beds and Structures", *AIChEJ* 2, p 393–403 (1956), and was stated in terms of percolation theory by Ambegaokar, V., et al. "Hopping Conductivity in Disordered Systems", *Phys. Rev. B.* 4, p 2612–2620 (1971). Quantitatively, the permeability controlling length scale, $l_c$, is obtained from $$p_c = \int_{l_c}^\infty n_l(l)dl \tag{9}$$

It may be assumed that the volume of a pore, V(l) is proportional to $l^\nu$ where $\nu$ is a geometric factor discussed in detail below. If the volume contained in the pore throats is neglected, and it is assumed that the nodes are the pores, $v$ will have a value of three for spherical pores. Given a monotonic mapping between pore sizes and the throat sizes associated with the pore, $p_c$ should correspond to that of the site percolation problem. Since the observed magnetization is often transformed to $g_o(T_{2o})$, $g_o$ can be used to compute $T_{2oc}$ (which is the critical $T_{2o}$) according to $$p_c = \frac{\int_{T_{2oc}}^{\infty} T_{2o}^{-v}(T_{2b} - T_{2o})^v g_o(T_{2o}) dT_{2o}}{\int_0^{\infty} T_{2o}^{-v}(T_{2b} - T_{2o})^v g_o(T_{2o}) dT_{2o}} \qquad (10)$$

In equation (10), values must be chosen for $p_c$ and $v$. The critical percolation probability $p_c$ changes with lattice type, and is known to range from approximately 0.2 for an FCC (face centered cubic) lattice to approximately 0.3 for a simple cubic lattice. Shante, V. K. S. et al., "An Introduction to Percolation Theory", *Advanced Phys.* 20, p 325–357 (1971). In the absence of information, a value of approximately 0.25 is preferably used. On the other hand, depending upon the pore shape, the value $v$ may vary from 0 to 3. Ramakrishnan, T. S., et al., "Two-Phase Distribution in Porous Media: An Application of Percolation Theory", *Int. J. Multiphase Flow* 12(3), p 357–388 (1986).

Since the resistivity of a porous medium is affected largely by the porosity and the tortuosity of the pore connection, and only to a minor degree by the pore size distribution, the cementation exponent m may be assumed to increase monotonically with $p_c$, and be fairly independent of $g_l$ and $v$. The residual oil saturation ($S_{or}$), however, increases with both $v$ and $p_c$. Residual oil saturation also changes with $g_l$.

For in situ rocks (i.e., formations surrounding a borehole), it is virtually impossible to measure $p_c$ and $v$ directly. Rather, these values need to be inferred indirectly and to a large extent need to be obtained through modeling. As defaults, preferred values such as $v=2$ (cylindrical pores), and $p_c=0.25$ may be used. Alternatively, an experimental/data fitting procedure as shown in FIG. 1 may be helpful in estimating values for $p_c$ and $v$.

Figure 1:
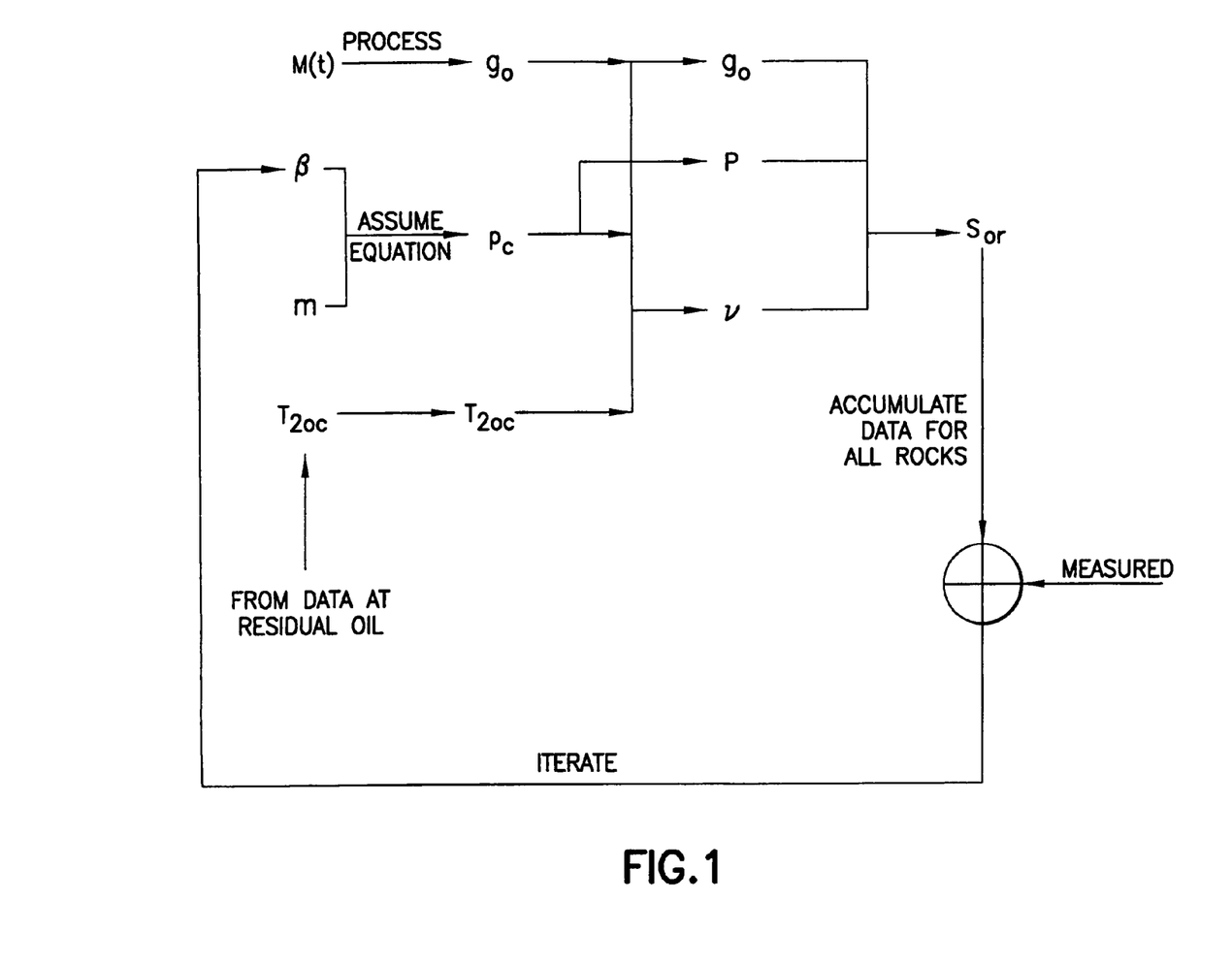
FIG. 1 is a flow chart illustrating a method of estimating a critical percolation probability $p_c$ and a rock structure geometric factor v.

As seen in FIG. 1, $S_{or}$, m and M(t) are treated as measured quantities, with M(t) being measured by an NMR tool, $S_{or}$ being obtained from any of several tools such as the MSFL or MCFL (trademarks of Schlumberger), and m being obtained e.g., from core measurements. The range for m is fairly narrow; typically between 1.7 and 2. The ratio of conductivity of rock to that of the saturating fluid is $\sigma/\sigma^w=\phi^m$. From M(t), as previously discussed, it is possible to solve for $g_o$ and $g_{wo}$. Alternatively, $g_o$ and $g_{wo}$ may be parametrized and optimized as well. Also, from M(t) in a fully water saturated sample at $S_{or}$, $T_{2oc}$ may be derived, as will be discussed in detail hereinafter. As seen in FIG. 1, $p_c$ is calculated using m and parameter(s) $\beta$, where any simple mathematical correlation may be assumed such that m increases with $p_c$ and the parameters of the fit are $\beta$. Given $p_c$, it can be assumed that the percolation probability P is known. Also, given $p_c$, $T_{2oc}$, and $g_o$, using equation (10), a value for $v$ can be calculated. From $v$, P and $g_o$, an estimate of $S_{or}$ may be obtained from a percolation-like model. See, e.g., Ramakrishnan, T. S. et al., "The Relative Permeability Function for Two-Phase Flow in Porous Media: Effect of Capillary Number", *Powder Technol.* 48, p 99–124 (1986); Ramakrishnan, T. S., et al., "Two-Phase Distribution in Porous Media: An Application of Percolation Theory", *Int. J. Multiphase Flow* 12(3), p 357–388 (1986). This estimated $S_{or}$ is then compared to the measured $S_{or}$ value, and an iteration is conducted for parameter(s) $\beta$. The comparison is jointly done with prefereably all of the rock data, with a universal set for parameter(s) $\beta$. Thus, each rock will have its own value of m, $g_o$, $v$, and $S_{or}$, but the functional relationships for $p_c$ versus m, and for $S_{or}$ in terms of $p_c$, $g_o$, and $v$ are expected to be universal.

With values for $p_c$ and $v$, however obtained, equation (10) permits a calculation of $T_{2oc}$. From $T_{2oc}$, $T_{2ic}$ (the intrinsic critical T2) may be obtained according to $$T_{2ic} = \frac{T_{2oc} T_{2b}}{T_{2b} - T_{2oc}}. \qquad (11)$$

If it is assumed that the pore volume to surface ratio corresponds to that of a sphere, then $3l_c = r_c$, where $r_c$ is the pore radius. Assuming that the pore radius is proportional to the throat radius by a factor $\alpha \approx 3$, and translating a permeability formula of the type $$k = \frac{C}{F} r^2$$

(see, e.g., Macmullin, R. B. et al.—previously cited; Johnson, D. L. et al., "New Pore-Size Parameter Characterizing Transport in Porous Media", *Phys. Rev. Lett.* 57(20), p 2564–2567 (1986); Ramakrishnan, T. S. et al., *SPE49502* (1998)), where r is a permeability determining length scale, the following is obtained:

$$k \approx \frac{1}{72F} r_c^2 = \frac{l_c^2}{8F} \qquad (12)$$

where F is the formation factor defined according to $F=1/\phi^m$. The proportionality constant of $\frac{1}{8}$ may need minor adjustments for a given region or lithology, but in general, the result finds wide applicability. As shall be seen, the calibration methods of the invention compensate for any inaccuracies in this value. In terms of $T_{2oc}$, Equation 12 becomes $$k = \frac{1}{8F} \rho^2 \frac{T_{2oc}^2 T_{2b}^2}{(T_{2b} - T_{2oc})^2} \qquad (13)$$

where it is seen that the permeability is defined in terms of the surface relaxivity $\rho$. It should be appreciated that the numerical proportionality constant ($\frac{1}{8}$) may be lumped with $\rho^2$ in a calibration process as discussed hereinafter. It will also be appreciated that since $T_{2ic}$ is a function of $T_{2oc}$ (and $T_{2b}$), equation (13) can be rewritten in terms of $T_{2ic}$.

It should be appreciated by those skilled in the art that equation (13) which relates the permeability k to the surface relaxivity and the critical observed T2 ($T_{2oc}$c) permits a determination of permeability utilizing an NMR tool in a different manner than previously conducted in the art. In particular, in the past, no attempt was made to estimate surface relaxivity downhole or to measure $T_{2oc}$ in order to relate the two to obtain a determination of permeability. Because, as described hereinafter, the surface relaxivity is a function of lithology and the mineralogy of the medium, the determination of permeability using the surface relaxivity and $T_{2oc}$ provides improved results.

Permeability determinations obtained from drawdown tools may be used to calibrate measurements made by NMR tools because the length scale of investigation of a drawdown tool is typically comparable to the length scale of investigation of an NMR measurement (e.g., a radius of investigation of between 2 and 5 cm). Thus, for example, if an NMR measurement and an MDT permeability measurement are available in a water zone, a calibration value for $\rho$ may be obtained by rearranging equation (13) to solve for surface relaxivity $\rho$, and by substituting the drawdown permeability $k_{dd}$ for k, such that $$\rho = \sqrt{\frac{8k_{dd}}{\phi^m}} \frac{T_{2b} - T_{2oc}}{T_{2oc}T_{2b}}, \tag{14}$$

where the porosity term replaces F according to $F=1/\phi^m$ as previously stated. In the absence of additional information, the cementation factor m may be assumed to equal 2. Once a calibration for surface relaxivity $\rho$ is obtained, it may be used as the value for similar lithologies along the wellbore. Thus, according to the invention, once a value for $\rho$ is obtained for a particular lithology, the NMR determinations can be utilized to provide a continuous log of permeability for that lithology by finding $T_{2oc}$ and utilizing equation (13). It will also be noted that equation (14) can be rewritten to placed in terms of $T_{2ic}$ instead of $T_{2oc}$ (and $T_{2b}$).

Calibration in an oil zone is more complex. A multiprobe drawdown tool can be utilized to provide single phase permeability from multiprobe pressure data. The NMR measurement, however, is in a zone with water and trapped hydrocarbon (where filtrate invasion from a water-based mud has displaced oil and trapped residual oil). The corresponding T2 distribution for a water saturated rock cannot be inferred completely. Therefore, an understanding of the NMR response in such an environment is needed.

In the percolation process, whereby the wetting fluid sequentially advances into larger and larger pores, a stage is reached where an infinite cluster in the oil phase (assumed non-wetting) is broken and only finite clusters of oil remain. This is the point at which the formation consists of only the residual oil saturation and is the condition close to the borehole when water-based filtrate invades an oil formation. Mathematically, if the fraction of sites that water is allowed to occupy is p, when residual oil saturation is reached, $P(1-p)=0$, where P is the percolation probability. Larson, R. G. et al., "Effect of Sample Size on Capillary Pressure Curves in Porous Media", *Powder Technol.* 30, p 123–138 (1981); Ramakrishnan, T. S., et al., "The Relative Permeability Function for Two-Phase Flow in Porous Media: Effect of Capillary Number", *Powder Technol.* 48, p 99–124 (1986). In other words, p at $S_{or}$ is $1-p_c$. Therefore, as previously discussed, water would have occupied pores as large as those that correspond to the most resistant restriction in the least resistant pathway. This, to the leading order, is the pore that determines permeability. Thus, in many ways, calibration of NMR with MDT is easier in a two-phase environment than with single phase because a signature of the permeability governing pore size is left by the trapping process. This is an important step in being able to compute permeability from measurements obtained in a two-phase environment.

To take advantage of the physics of trapping in order to estimate the characteristic pore size, it is helpful to know a priori, the bulk relaxation behavior, $M_o(t)$ of the crude oil. $M_o(t)$ can be represented in terms of a finite number of exponentials:

$$M_o(t) = \sum_{k=1}^{N_o} a_{ko} \exp(-t/T_{2bo_k}) \tag{15}$$

where $a_{ko}$ is an oil constant for the k'th exponential, and $T_{2bok}$ is the spin—spin relaxation time of bulk oil for the k'th exponential. In order that the resolution of the relaxation behavior be robust, the number $N_o$ should be small (e.g., 1 to 3). Then the observed magnetization in the presence of trapped hydrocarbon is $$M(t) = \phi(1-S_{or}) \int_0^\infty g_{wo}(T_{2o}) \exp(-t/T_{2o}) dT_{2o} + \phi S_{or} \sum_{k=1}^{N_0} a_{ko} \exp(-t/T_{2bo_k}) \tag{16}$$

where $g_{wo}$ is the volume probability density function of water occupied pores with respect to $T_{2o}$. Those skilled in the art will appreciate that the first term of the right side of equation (16) is the contribution by protons in water, and the second term of the right side of equation (16) is the contribution of the bulk relaxation of oil. Based on the water-oil phase replacement physics as described above, the critical observed T2 is $$T_{2oc} = \max \arg\{g_{wo}(T_{2o})\} : g_{wo} > 0 \tag{17}$$

In practice, the inversion for $g^{wo}$ is susceptible to spreading due to finite signal to noise ratio and the ill-conditioned nature of the inversion problem. For this reason, a preferable choice is to estimate $T_{2oc}$ from $$x = \int_0^{T_{2oc}} g_{wo}(T_{2o}) dT_{2o} \tag{18}$$

where x is a number close to 1 (e.g., 0.9). In the application of equation (16), available resistivity data for $S_{or}$ may be utilized. Alternatively, $S_{or}$ may be permitted to float as a part of an inversion. In either case, any error in the characterization of oil relaxation should not cause significant errors in $T_{2oc}$ by using an x somewhat smaller than unity. Alternatively, during the processing for $g_{wo}$, one may allow for progressively smaller noise in the data, estimate $T_{2oc}$ successively, and extrapolate for $T_{2oc}$ in the limit of zero noise.

Once the $T_{2oc}$ computation is carried out, the surface relaxivity $\rho$ can be calibrated using the horizontal dual probe permeability $k_{hdp}$ from a dual probe interpretation (see Goode, P. et al., *SPE Formation Evaluation* 11, p 31–40 (1996) and modifying equation (14) according to:

$$\rho = \sqrt{\frac{8k_{hdp}}{\phi^m}} \frac{T_{2b} - T_{2oc}}{T_{2oc}T_{2b}} \tag{19}$$

As before, the calibrated value of this $\rho$ can be used to determine a NMR based permeability in other lithologically similar regions according to $$k = \frac{\phi^m}{8}\rho^2 \frac{T_{2oc}^2 T_{2b}^2}{(T_{2b} - T_{2oc})^2}. \quad (20)$$

It should be noted that in lieu of multiprobe testing, a dual-packer module may be used, and the single phase horizontal permeability interpretation of the packer or the packer-probe combination may be substituted for $k_{hdp}$. Because the length scale over which the MDT estimates are thought to be representative are much larger than that applicable for the NMR analysis, in order to make a fair comparison, the simplest solution is to average the NMR permeability-layer thickness product as given by equation (20) and then compare it with the MDT values. To do this, the layer thicknesses should be known, and $\rho$ should be assumed to be constant over the interval.

In some cases in an oil zone, only single probe drawdown data may be available from a tool such as the MDT. In these cases, calibration for surface relaxivity is even more difficult. In particular, from the drawdown pressure data of the MDT, only the effective permeability to water at residual oil conditions is available. It is then necessary to relate that effective permeability to surface relaxivity. In order to do that, an understanding of the network physics is helpful.

A network in which the residual oil saturation is present along with water is imagined. For invasion depths observed in practice, it is reasonable to assume that the measured drawdown permeability is $k^0_{ew} = k k^0_{rw}$, where $k^0_{rw}$ is the relative permeability to water at a water saturation=$1-S_{or}$. The relative permeability may be substantially smaller than unity.

As in the previous case, it can be assumed that an inversion for $g_{wo}(T_{2o})$ has been carried out. Analogous to the case of single phase permeability, $k^0_{rw}$ can be calculated as a function of the critical radius and the formation factor in a mixed saturation state according to:

$$k^0_{ew} = \frac{l^2_{wc}}{8 F_w} \quad (21)$$

By definition, $l_{wc}$ is the volume to surface area of the most resistant pore in the least resistant path among the pores containing bulk water (as opposed to thin films of water), and $F_w$ is the formation factor that may be approximated through the Archie relation $$F_w = \frac{1}{\phi^m S_w^n}. \quad (22)$$

Often, m is equated to n if no other information is available. The difficulty therefore lies in determining $l_{wc}$.

Recognizing that a subnetwork of the original lattice is occupied by water, a critical percolation probability for the water-occupied pores may be defined as $p_{cw}$ by modifying equation (10) according to $$p_{cw} = \frac{\int_{T_{2woc}}^{T_{2oc}} T_{2o}^{-\nu}(T_{2b} - T_{2o})^{\nu} g_{wo}(T_{2o}) dT_{2o}}{\int_0^{T_{2oc}} T_{2oc}^{-\nu}(T_{2b} - T_{2o})^{\nu} g_{wo}(T_{2o}) dT_{2o}}. \quad (23)$$

It should be noted that the entire water occupied network has pores up to $T_{2oc}$, the point at which oil is completely trapped. In this network, the above equation allows for a calculation of $T_{2woc}$, which in turn determines the critical pore size governing water mobility.

It should be noted that extensive tabulations for $p_c$ are available for a variety of lattices whereas tabulations for $p_{cw}$ are generally unavailable. To calculate $p_{cw}$, the following steps should be carried out:

a) start with the lattice of interest;

b) carry out an invasion percolation algorithm (Wilkinson, D. et al., "Invasion Percolation: A New Form of Percolation Theory", *J. Phys. A: Math. Gen* 16, p 3365–3376 (1983), modified for trapping, or a phase replacement algorithm as per ordinary percolation in which members from isolated clusters are not allowed to be removed (Ramakrishnan, T. S., et al., "Two-Phase Distribution in Porous Media: An Application of Percolation Theory", *Int. J. Multiphase Flow* 12(3), p 357–388 (1986);

c) continue until only isolated clusters remain;

d) arbitrarily color the isolated clusters a first color and the remaining lattice members a second color;

e) start with only the remaining members as the parent lattice. Physically, this lattice represents the percolating water cluster. The first color members are voided out and presumed nonexistent;

f) carry out an ordinary percolation algorithm on the second color lattice until no infinite clusters remain. The number fraction of the members in the remaining second color lattice with respect to the parent lattice members provides $p_{cw}$. This may be carried out for all standard lattices. The calculation is independent of the pore size distribution.

A rough estimate of $p_{cw}$ may be made by looking at the results for Bethe lattices. For these lattices, as set forth in Shante, V. K. S., et al., "An Introduction to Percolation Theory", *Advanced Phys.* 20, p 325–357 (1971), $$p_c = \frac{1}{z-1} \quad (24)$$

where z is the coordination number. At residual oil condition, the coordination number of the water percolating network can be approximated as $z(1-1/(z-1))=z(z-2)/(z-1)$. For this new coordination number, replacing z in equation (24) with $z(z-2)/(z-1)$, an estimate for $p_{cw}$ is $$p_{cw} \approx \frac{z-1}{z^2 - 3z + 1}. \quad (25)$$

Clearly, the Bethe lattice result cannot be applied to the well known 3D lattices in terms of the coordination number. But, the ratio $p_{cw}/p_c$ of the Bethe lattice should be applicable. Then, $$p_{cw} \approx p_c \frac{(z-1)^2}{z^2 - 3z + 1} \quad (26)$$

Applying this result for an FCC lattice, the following result is obtained:

$$p_{cw} \approx 1.1 p_c \quad (27)$$

Even for a simple cubic lattice, $p_{cw}$ is expected to be only 30% larger than $p_c$. Therefore, $p_{cw}$ is expected to lie in the range of 0.2 to about 0.4.

From equation (23), $T_{2woc}$ can be calculated. Comparing equation (13) with equation (21), the effective permeability to water is written as $$k_{ew}^0 = \frac{1}{8 F_w} \rho^2 \frac{T_{2woc}^2 T_{2b}^2}{(T_{2b} - T_{2woc})^2}. \quad (28)$$

Given that $k^0_{ew}$ is known from single probe MDT data, a calibration for $\rho$ is obtained, which may then be used to generate a continuous log for $k^0_{ew}$. More importantly, since $T_{2oc}$ has also been generated in this process, it is possible to compute single phase permeability from NMR measurement in a two-phase environment through $$k = \frac{\phi^m}{8} \rho^2 \frac{T_{2oc}^2 T_{2b}^2}{(T_{2b} - T_{2oc})^2}. \quad (29)$$

Equation (29) shows that NMR and MDT data influenced by the presence of two immiscible phases can be used to determine single phase permeability.

Even in the absence of MDT permeability, equation (29) can be used provided that values of $\rho$ are known a priori for the region of interest. The estimate using equation (29) takes into account the network physics. Indeed, in contrast to the methods of the prior art that are hindered by the presence of hydrocarbon, the present invention takes full advantage of the basic physics of the problem to obtain the correct $T_{2oc}$ to be used in the permeability determination. In many ways, the interpretation is actually facilitated by the presence of hydrocarbon, because the estimation procedure for $T_{2oc}$ requires only the known bulk relaxation characteristics of oil.

Figure 2:
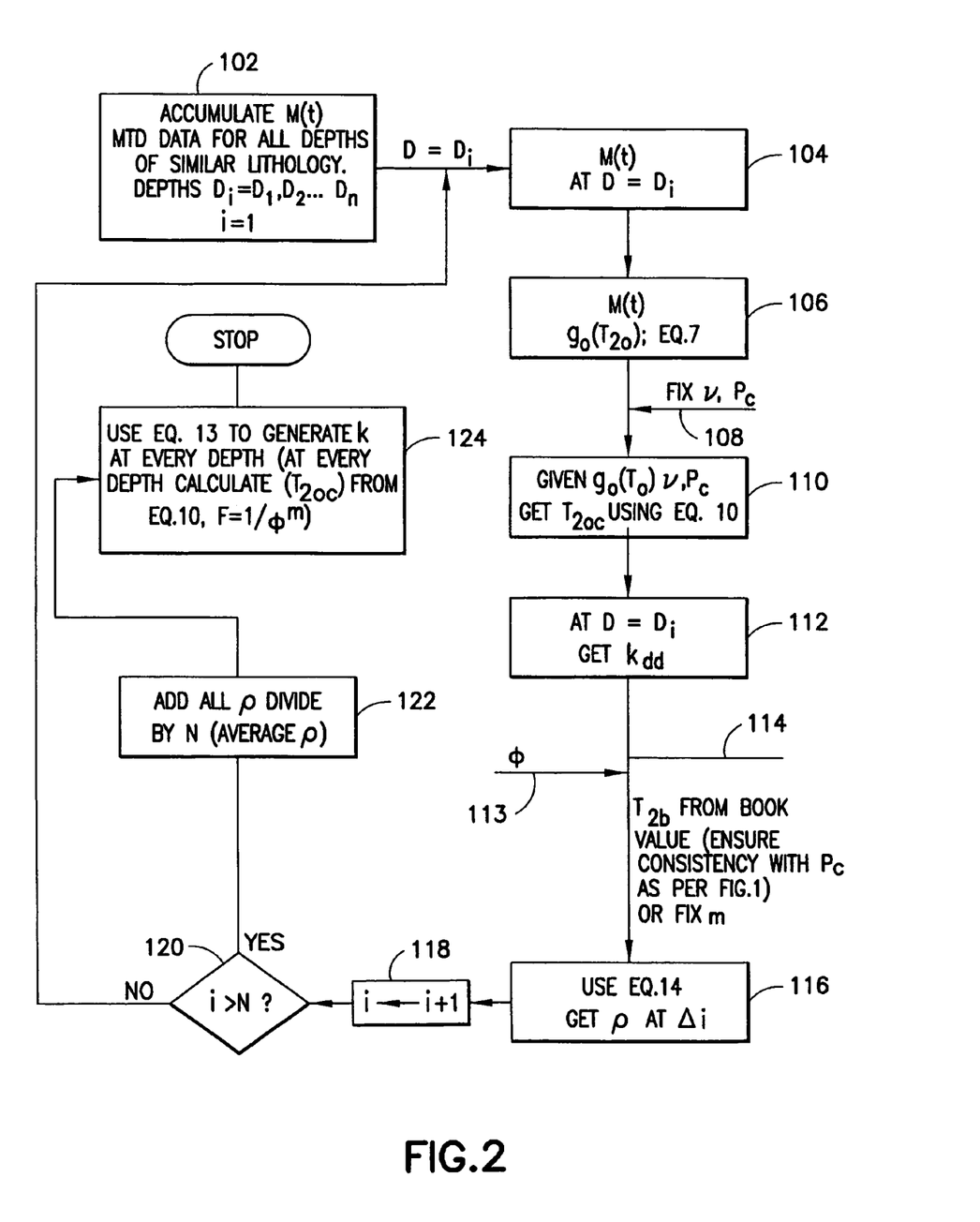
FIG. 2 is a flow chart illustrating a first embodiment of a method for determining formation permeability utilizing an NMR tool.

Given the understanding set forth above it is possible to generate a permeability log along a formation traversed by a borehole. More particularly, as seen in FIG. 2, and with respect to water zones of the formation, at 102 data from a drawdown tool such as the MDT tool and from an NMR tool such as the CMR or MRX is obtained. The data from the drawdown tool may be from a single water zone depth in the formation or from one or more water zone depths $D_i = D_1, D_2, D_3 \ldots D_N$ of similar lithology. The information from the NMR tool is indicated as M(t), and this information may be more or less continuous along the length of the borehole or in the zones of interest. For a first MDT sampling depth i=1, at 104, the NMR derived measurement M(t) is obtained. At 106, from M(t), a value for $g_o(T_{2o})$ can be obtained using equation (7). Then, at 108, either using the method of FIG. 1, or based on other known information, or based on default values, values for v and $p_c$ are selected. Once values for $g_o(T_{2o})$, v, and $p_c$ are provided, at 110, a determination of $T_{2oc}$ is made using equation (10). Then, at 112, the drawdown permeability $k_{dd}$ for the depth $D_i$ is obtained from the drawdown tool, at 113, the porosity for the depth $D_i$ is obtained from previous information, from other borehole tools, or from the NMR or drawdown tools, and at 114, values for $T_{2b}$ and m are selected. The value for $T_{2b}$ for water is typically known from literature, while m is either fixed or selected to ensure consistency with $p_c$ as previously discussed with reference to FIG. 1. In any event, with the determination of $T_{2oc}$, and values for $k_{dd}$, $T_{2b}$, m, and $\phi$ provided, the surface relaxivity $\rho$ is computed at 116 using equation (14). At 118, the index i is increased (i.e., i=i+1), and at 120, the increased index is compared to the number N of depths that MDT data was taken for water zones of similar lithology. If data for all MDT sampling depths $D_i$ have not been processed, the method continues at step 104 for the next depth. If data for all depths has been processed, then at 122, the surface relaxivity $\rho$ for the lithology of interest is computed by averaging the surface relaxivities found at 116 (e.g., by adding the values for each depth and dividing by the number N of depths). It will be appreciated that where only one drawdown data point is available, steps 104–120 are conducted only once, and there will be no averaging at step 122. In any event, with a value for the surface relaxivity $\rho$ having been obtained, the permeability k for any depth of similar lithology is obtained at 124 utilizing the NMR data and equation (13) for each depth of interest. For example, if depth $D_i$ at which MDT data was obtained was in a particular stratum of the earth formation, permeability determinations are made not only for depth $D_1$, but at multiple locations (e.g., $D_{1-1}, D_{1-2}, D_{1-3}, D_{1-4} \ldots D_{1-Z}$, where Z is a positive integer) in that stratum depending upon the resolution of the NMR tool. So, for each of the Z borehole depths or locations in the stratum for which an NMR values M(t) are obtained, a separate value for the critical observed spin—spin time $T_{2oc}$ is calculated according to equation (10), and this value is used in equation (13) in conjunction with the surface relaxivity $\rho$ for that lithology in order to obtain Z calculations of permeability. The calculations of permeability may then be displayed in log format as is well known in the art. Similarly, for other strata of similar lithology, the NMR measurements M(t) are used to calculate values of $T_{2oc}$ using equation (10), and those values are used in conjunction with the surface relaxivity $\rho$ for that lithology in equation (13) to obtain determinations of permeability k which may be displayed in log format.

Those skilled in the art will appreciate that mineralogists will generally agree on what constitutes zones of "similar lithology", and that the determinations made according to the invention will be less accurate when the surface relaxivity utilized to determine the permeability relates to a zone which is less similar. More particularly, in applying the methods of the invention to zones of "similar lithology", it will be appreciated that the first order or primary consideration is whether the zones have similar mineralogy; e.g., limestone, sandstone, dolomite, and relative clay components. A second order consideration would be the deposition environment. Information regarding mineralogy may be obtained using downhole tools such as the ECS (Elemental Capture Sonde) tool or the FMI borehole imaging tool (ECS and FMI being trademarks of Schlumberger). Thus, where the mineralogy between zones is similar, it can be expected that the permeability determinations will be relatively good regardless of deposition environment. However, determinations made in zones of similar mineralogy and similar deposition environment will typically be better than determinations made in zones of similar mineralogy and different deposition environment.

Figure 3:
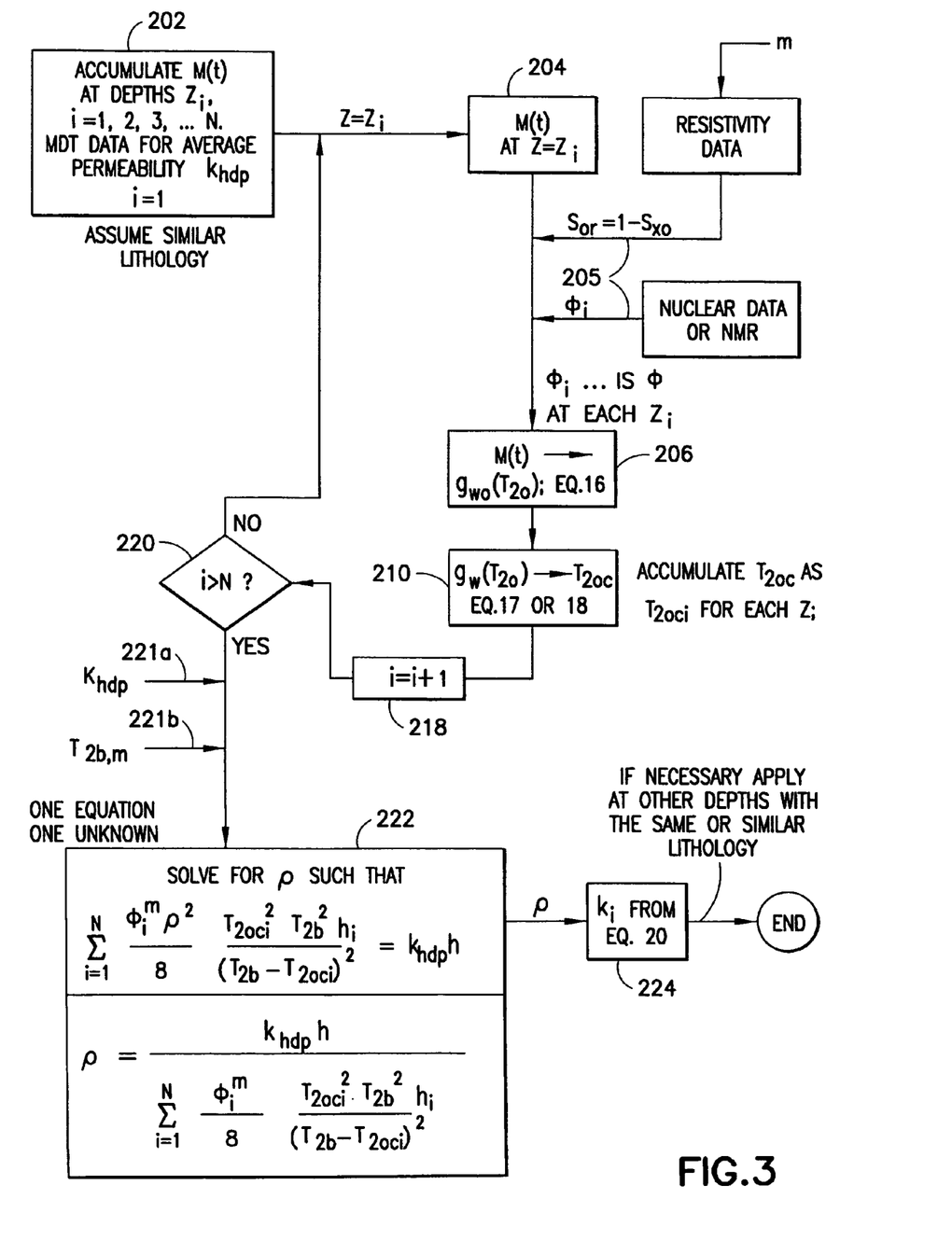
FIG. 3 is a flow chart illustrating a second embodiment of a method for determining formation permeability utilizing an NMR tool.

Turning now to FIG. 3, a second embodiment of the invention is seen with respect to oil zones of the formation where horizontal permeability data is available from either a dual probe drawdown tool, or a packer or packer-probe tool (hereinafter referred to as MDT data for this embodiment). In the second embodiment, at 202 MDT data and data from an NMR tool such as the CMR or MRX is obtained. The data from the MDT is indicated as being from a single location in an oil zone in the formation, while the information M(t) from the NMR may be more or less continuous in the zone of investigation of the MDT (i.e., at various depths $Z_i$ which are typically anywhere between 0.1 and 0.5 meters apart over the expected depth of investigation of the MDT multiprobe tool). For a first depth i=1, at 204, the NMR derived measurement M(t) is obtained. At 205, porosity $\phi$ and residual oil saturation $S_{or}$ data is provided for that depth. The data provided at 205 may be obtained from one or more of (i) the MDT tool, (ii) other tools which measure formation resistivity and/or porosity, (iii) the NMR tool, or (iv) previously obtained knowledge of the formation. In any event, at 206, utilizing M(t), $\phi$, and $S_{or}$, a value for $g_{wo}(T_{2o})$ is obtained using equation (16). From $g_{wo}(T_{2o})$, using either equation (17) or equation (18), a determination of $T_{2oc}$ is made at 210. Then, at 218, the NMR depth index i is increased and at 220 the increased index is compared to N to see whether all NMR data for the depth of interest have been analysed. If not, the method returns to step 204 and cycles through until all data samples have been analysed. If so, at 221a, the horizontal dual probe permeability $k_{hdp}$ for the depth $Z_i$ (or, in the case of a dual-packer module or a packer-probe combination, a single phase horizontal permeability interpretation for that depth) is obtained from the MDT. At 221b, values for $T_{2b}$ and m are selected. The value for $T_{2b}$ (for water) is typically known from literature, while m is either fixed or selected to ensure consistency with $p_c$ as previously discussed with reference to FIG. 1. In any event, with the determinations of $T_{2oc}$ at the different depths $Z_i$ ($T_{2oci}$) as calculated at step 210, and depth dependent values for porosity $\phi_i$, and values for $k_{hdp}$, $T_{2b}$, and m provided, the surface relaxivity $\rho$ is computed at 222. The computation at 222 uses a modification to equation (19) which sums the equation over depths $Z_i$ to $Z_n$ by multiplying a calculated value by values of depth intervals $h_i$ (i.e., $h_i = Z_n - Z_{n-1}$) over the depth of investigation, and dividing by the total depth of investigation of the MDT tool ($h = Z_n - Z_1$).

With a value for the surface relaxivity $\rho$ having been obtained, the permeability k for the depths $Z_i$ through $Z_N$ are individually obtained at 224 using equation (20) for each depth with $\phi$ being the porosity for that depth and the observed critical T2 being the $T_{2oc}$ as calculated at step 210 according to equations (17) or (18) for that depth. The calculations of permeability may then be displayed in log format as is well known in the art. Similarly, for other locations of similar lithology (in the same stratum or in different strata), the NMR measurements M(t) are used to calculate values of $T_{2oc}$ using equation (17) or equation (18), and those values may be used in conjunction with the surface relaxivity $\rho$ for that lithology in equation (20) to obtain determinations of permeability k which may be displayed in log format.

It should also be appreciated by those skilled in the art that if the multiprobe MDT is located such that its probes are in different strata such that the obtained permeability determination $k_{hdp}$ is effectively an average of different permeabilities, it is possible to deconvolve the permeability information.

Figure 4:
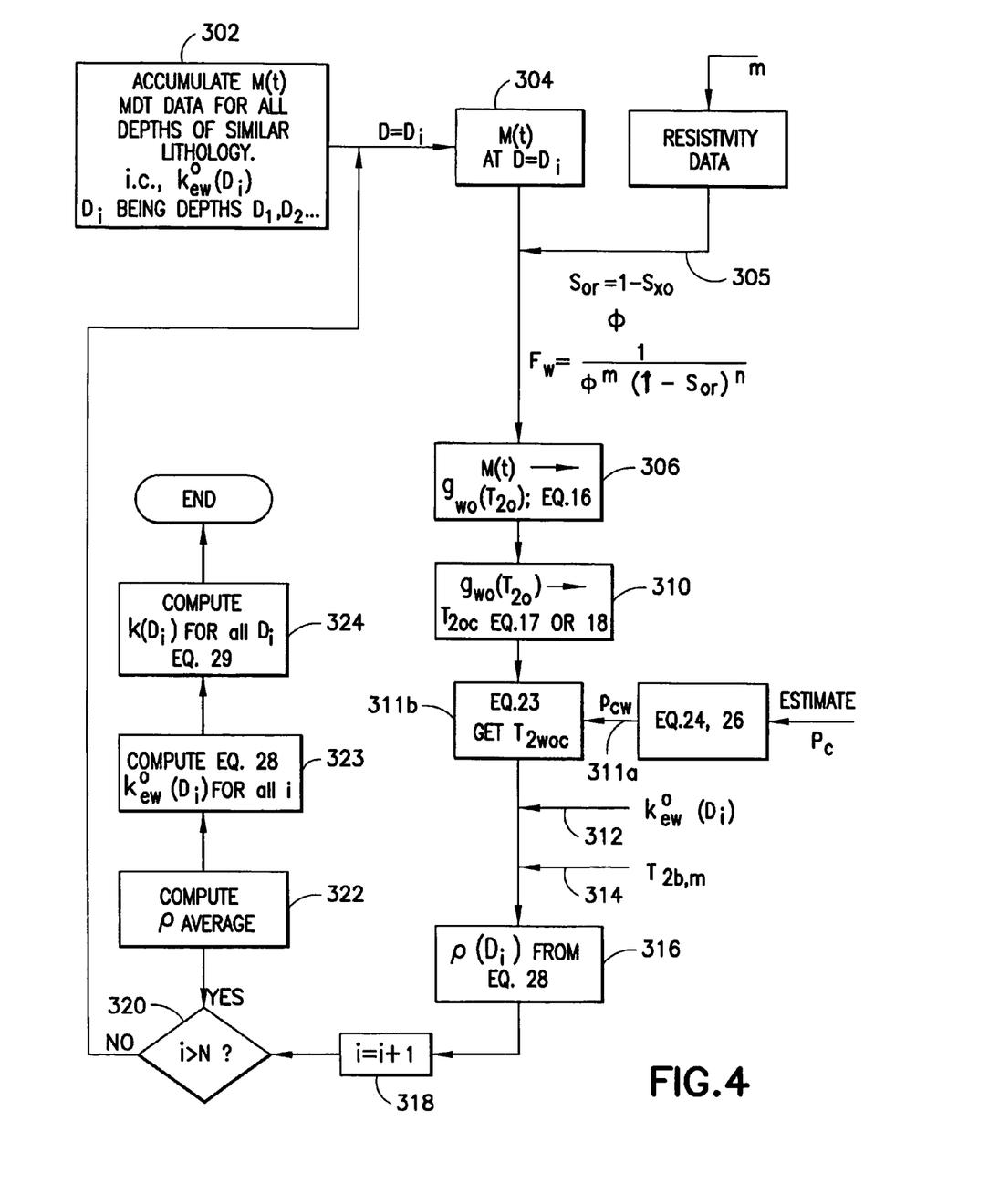
FIG. 4 is a flow chart illustrating a third embodiment of a method for determining formation permeability utilizing an NMR tool.

Turning now to FIG. 4, a third embodiment of the invention is seen with respect to oil zones of the formation where drawdown data is available from a single probe tool. At 302 data from a drawdown tool such as the MDT tool and from an NMR tool such as the CMR or MRX is obtained. The data from the drawdown tool may be from a single oil zone depth in the formation or from one or more oil zone depths $D_i = D_1, D_2, D_3 \ldots D_N$ of similar lithology. The information from the NMR tool is indicated as M(t), and this information may be more or less continuous along the length of the borehole or in the zones of interest. For a first MDT sampling depth i=1, at 304, the NMR derived measurement M(t) is obtained. At 305, porosity $\phi$ and residual oil saturation $S_{or}$ data is provided for that depth. The data provided at 305 may be obtained from one or more of (i) the MDT tool, (ii) other tools which measure formation resistivity and/or porosity, (iii) the NMR tool, or (iv) previously obtained knowledge of the formation. In any event, at 306, from M(t), a value for $g_{wo}(T_{2o})$ can be obtained using equation (16). Then, from $g_{wo}(T_{2o})$, using either equation (17) or equation (18), a determination of $T_{2oc}$ is made at 310. At 311a, a value for $p_{cw}$ is obtained either based on other known information, or based on default values, or based on an estimate of $p_c$ and the use of equations (24) and (26). An estimated value for $p_c$ (and v) can be made using the method of FIG. 1, or based on other known information, or based on default values. Once values for $g_{wo}(T_{2o})$, v, and $p_{cw}$ are provided, at 311b, a determination of $T_{2woc}$ is made using equation (23). Then, at 312, the drawdown permeability $k^o_{ew}$ for the depth $D_i$ is obtained from the drawdown tool, and at 314, values for $T_{2b}$ and m are selected. The value for $T_{2b}$ for water is typically known from literature, while m is either fixed or selected to ensure consistency in $p_c$ as previously discussed with reference to FIG. 1. In any event, with the determination of $T_{2woc}$, and values for $k^o_{ew}$, $T_{2b}$, and m and $\phi$ (needed to calculate $F_w$) provided, the surface relaxivity $\rho$ is computed at 316 using equation (28). At 318, the index i is increased (i.e., i=i+1), and at 320, the increased index is compared to the number N of depths that MDT data was taken for water zones of similar lithology. If data for all MDT sampling depths $D_i$ have not been processed, the method continues at step 304 for the next depth. If data for all depths has been processed, then at 322, the surface relaxivity $\rho$ for the lithology of interest is computed by averaging the surface relaxivities found at 316 (e.g., by adding the values for each depth and dividing by the number N of depths). It will be appreciated that where only one drawdown data point is available, steps 304–320 are conducted only once, and there will be no averaging at step 322. In any event, with a value for the surface relaxivity $\rho$ having been obtained, if desired, at 323, the effective permeability to water $k^o_{ew}$ may be generated for all depths $D_i$ using the NMR data for that depth and utilizing equation (28) and the determinations (i.e., $T_{2oc}$) at that depth utilized in equation (28). If desired, $k^o_{ew}$ may be displayed as a continuous log. In addition, at step 324, using the surface relaxivity found at 322 as well as $T_{2oc}$, $T_{2b}$, m and $\phi$, the permeability k is found for each depth $D_i$ using equation (29). Further, determinations of permeability for locations of similar lithology are obtained at 324 utilizing the NMR data and equation (29) for each depth of interest. For example, if depth $D_1$ at which MDT data was obtained was in a particular stratum of the earth formation, permeability determinations are made not only for depth $D_1$, but at multiple locations (e.g., $D_{1-1}$, $D_{1-2}$, $D_{1-3}$, $D_{1-4}$ ... $D_{1-Z}$, where Z is a positive integer) in that stratum depending upon the resolution of the NMR tool. So, for each of the Z borehole depths or locations in the stratum for which an NMR values M(t) are obtained, a separate value for the critical observed spin—spin time $T_{2oc}$ is calculated according to equation (17) or equation (18), and this value is used in equation (29) in conjunction with the surface relaxivity ρ for that lithology in order to obtain Z calculations of permeability. The calculations of permeability may then be displayed in log format as is well known in the art. Similarly, for other strata of similar lithology, the NMR measurements M(t) are used to calculate values of $T_{2oc}$ using equation (17) or equation (18), and those values are used in conjunction with the surface relaxivity ρ for that lithology in equation (29) to obtain determinations of permeability k which may be displayed in log format.

As set forth above, given both drawdown and NMR type information, the present invention permits determinations of surface relaxivities for different lithologies. In addition, using NMR tool measurements in conjunction with the relaxivity information, the invention allows the calculation of permeability at points along the formation for which NMR tool measurements have been made but where no drawdown information is available. Thus, provided that surface relaxivity determinations are made for all zones of interest along the borehole (i.e., all lithologies of interest), it will be appreciated that a substantially continuous permeability log can be generated for those zones along the borehole.

There have been described and illustrated herein methods for determining permeability from NMR measurements. While particular embodiments of the invention have been described, it is not intended that the invention be limited thereto, as it is intended that the invention be as broad in scope as the art will allow and that the specification be read likewise. Thus, while the invention was described with reference to utilizing information obtained from a "drawdown" type tool such as the MDT, for purposes of the invention, a "drawdown tool" should be understood to be any tool which permits fluid to flow into and/or out of the tool, and therefore, out of and/or into the formation. Thus, for purposes herein, drawdown tools shall be understood to include injection type tools. It will also be appreciated that while according to the preferred embodiment, drawdown tools are used to obtain in situ permeability determinations, other means could be utilized to generate permeability determinations for calibration. For example, it is known in the art to use acoustic methods which use Stonely waves in order to make a determination of permeability. It is also known to conduct well test for direct production of hydrocarbons and to determine permeability of zones therefrom. According to the present invention, either of these, or any other in situ permeability determination could be utilized to generate permeability determinations for calibration with the NMR determinations. Further, it should be appreciated that while particular equations have been provided for calculating parameters, (e.g., $T_{2oc}$), the equations are generally zeroth order expressions, and the equations could be modified to add first and higher order corrections. By way of example and not limitation, equations (1) and (2) could be modified to account for diffusion in the pore. Similarly, by way of example and not limitation, equations (13) and (14) could be modified to account for first order changes which might affect the constant, or might provide additional parameters to the equation. Thus, for purposes of the invention, when a determination or calculation is made "substantially" according to an equation, it is intended that those skilled in the art could modify constants and/or make first or higher order changes to the equation. Also, while flow-charts were provided for carrying out the methods of the invention, it will be appreciated that various steps of the invention can be combined by combining various equations, etc. It will therefore be appreciated by those skilled in the art that yet other modifications could be made to the provided invention without deviating from its spirit and scope as claimed.

What is claimed is:

1. A method of investigating an earth formation traversed by a borehole by utilizing a nuclear magnetic resonance (NMR) tool, said method comprising:

using measurements obtained from the NMR tool which has been in the borehole, computing a surface relaxivity for a lithology in the formation; and generating a determination of permeability of a location in said earth formation as a function of said surface relaxivity and said measurements, wherein said computing a surface relaxivity comprises finding a critical observed spin—spin relaxation time ($T_{2oc}$) or a function thereof for said location and using said $T_{2oc}$ or said function thereof in computing said surface relaxivity.

2. A method according to claim 1, wherein:

said computing a surface relaxivity comprises utilizing a permeability determination of a drawdown tool which investigated said location or a location of similar lithology in the formation.

3. A method according to claim 2, further comprising:

generating additional determinations of permeability of a plurality of locations in said earth formation of a same or similar lithology to said location as a function of said measurements of said NMR tool corresponding to each of said plurality of locations and as a function of said surface relaxivity.

4. A method according to claim 3, further comprising:

plotting said additional determinations of permeability in log format as a function of location in said borehole.

5. A method according to claim 3, wherein:

said generating additional determinations comprises determining each additional determination substantially according to $$k_i = \frac{1}{8F_i} \rho^2 \frac{T_{2oci}^2 T_{2b}^2}{(T_{2b} - T_{2oci})^2}$$

where ρ is said surface relaxivity, $T_{2b}$ is a bulk transverse relaxation of water, and i is an index of said plurality of locations such that $k_i$ is the permeability at the i'th of said plurality of locations, $F_i$ is the formation factor at the i'th of said plurality of locations and $T_{2oci}$ is the $T_{2oc}$ at the i'th of said plurality of locations.

6. A method according to claim 1, wherein:

said function of $T_{2oc}$ is $T_{2ic}$, an intrinsic critical T2.

7. A method according to claim 2, wherein:

said lithology is in a water zone.

8. A method according to claim 7, wherein:

said computing a surface relaxivity comprises computing said surface relaxivity substantially according to $$\rho = \sqrt{\frac{8k_{dd}}{\phi^m}} \frac{T_{2b} - T_{2oc}}{T_{2oc}T_{2b}},$$

where ρ is said surface relaxivity, $k_{dd}$ is said permeability determination, $T_{2b}$ is a measure of bulk transverse relaxation of water, φ is a porosity of said formation at said location, and m is a cementation index of said formation at said location.

9. A method according to claim 8, wherein:
finding a critical observed spin—spin relaxation time ($T_{2oc}$) for said location comprises finding said $T_{2oc}$ substantially according to $$p_c = \frac{\int_{T_{2oc}}^{\infty} T_{2o}^{-\nu}(T_{2b} - T_{2o})^{\nu} g_o(T_{2o}) dT_{2o}}{\int_0^{\infty} T_{2o}^{-\nu}(T_{2b} - T_{2o})^{\nu} g_o(T_{2o}) dT_{2o}}$$

where $p_c$ is a critical percolation probability, $T_{2o}$ is an observed spin—spin decay made by the NMR tool, $T_{2b}$ is a measure of bulk transverse relaxation of water, $g_o$ is a probability density function, and ν is a geometric factor related to the formation at said location.

10. A method according to claim 9, wherein:
said generating a determination of permeability of a location comprises generating said determination substantially according to $$k = \frac{1}{8F} \rho^2 \frac{T_{2oc}^2 T_{2b}^2}{(T_{2b} - T_{2oc})^2}$$

where k is said determination of permeability, and F is a formation factor.

11. A method according to claim 10, further comprising:
generating additional determinations of permeability of a plurality of locations in said earth formation of a same or similar lithology to said location as a function of said measurements of said NMR tool corresponding to each of said plurality of locations and as a function of said surface relaxivity.

12. A method according to claim 11, further comprising:
plotting said additional determinations of permeability in log format as a function of location in said borehole.

13. A method according to claim 11, wherein:
said generating additional determinations comprises determining each additional determination substantially according to $$k_i = \frac{1}{8F_i} \rho^2 \frac{T_{2oci}^2 T_{2b}^2}{(T_{2b} - T_{2oci})^2}$$

where $T_{2b}$ is a bulk transverse relaxation of water, and i is an index of said plurality of locations such that $k_i$ is the permeability at the i'th of said plurality of locations, $F_i$ is the formation factor at the i'th of said plurality of locations and $T_{2oci}$ is the $T_{2oc}$ at the i'th of said plurality of locations.

14. A method according to claim 7, wherein:
said computing a surface relaxivity comprises, for said location and each location of similar lithology for which a drawdown tool permeability determination has been made, calculating respective surface relaxivities substantially according to $$\rho_{D_i} = \sqrt{\frac{8k_{ddD_i}}{\phi_{D_i}^m}} \frac{T_{2b} - T_{2oc_{D_i}}}{T_{2oc_{D_i}} T_{2b}},$$

where Di is a depth index for said location and said each location of similar lithology, and determining said surface relaxivity ρ as an average of said respective surface relaxivities.

15. A method according to claim 14, wherein:
said generating a determination of permeability of a location comprises generating said determination substantially according to $$k = \frac{1}{8F} \rho^2 \frac{T_{2oc}^2 T_{2b}^2}{(T_{2b} - T_{2oc})^2}$$

where k is said determination of permeability, and F is the formation factor.

16. A method according to claim 15, further comprising:
generating additional determinations of permeability of a plurality of locations in said earth formation of a same or similar lithology to said location as a function of said measurements of said NMR tool corresponding to each of said plurality of locations and as a function of said surface relaxivity.

17. A method according to claim 16, further comprising:
plotting said additional determinations of permeability in log format as a function of location in said borehole.

18. A method according to claim 2, wherein:
said lithology is an oil zone.

19. A method according to claim 18, wherein:
said drawdown tool is one of a multiprobe tool, a dual packer tool, and a packer-probe tool and provides a drawdown tool permeability determination over a length h of the borehole.

20. A method according to claim 19, wherein:
said computing a surface relaxivity comprises computing said surface relaxivity substantially according to $$\rho^2 = \frac{k_{hdp}h}{\sum_{i=1}^{N} \frac{\phi_i^m}{8} \frac{T_{2oci}^2 T_{2b}^2 h_i}{(T_{2b} - T_{2oci})^2}},$$

where ρ is said surface relaxivity, $k_{hdp}$ is said drawdown tool permeability determination, $T_{2b}$ is a measure of bulk transverse relaxation of water, i is an index of locations along said length h for which determinations are made by said NMR tool such that $h_i$ are respective locations, $\phi_i$ are respective porosities of said formation at said locations, $T_{2oci}$ are respective critical observed spin—spin relaxation times, and m is a cementation index.

21. A method according to claim 20, wherein:
said critical observed spin—spin relaxation time ($T_{2oc}$) for each of said locations is obtained by finding a $T_{2oc}$ for a respective location substantially according to either $x = \int_0^{T_{2oc}} g_{wo}(T_{2o}) dT_{2o}$ or $T_{2oc} = \max \arg\{g_{wo}(T_{2o})\} : g_{wo} > 0$ where $T_{2o}$ is an observed spin—spin decay made by the NMR tool for the respective location, x is a value close to 1, and $g_{wo}$ is the volume probability density function of water occupied pores with respect to $T_{2o}$.

22. A method according to claim 21, wherein:
said generating a determination of permeability of a location comprises generating said determination substantially according to $$k = \frac{1}{8F}\rho^2 \frac{T_{2oc}^2 T_{2b}^2}{(T_{2b} - T_{2oc})^2}$$

where k is said determination of permeability, and F is the formation factor.

23. A method according to claim 22, further comprising:
generating additional determinations of permeability of a plurality of locations in said earth formation of a same or similar lithology along said length as a function of said measurements of said NMR tool corresponding to each of said plurality of locations along said length and as a function of said surface relaxivity.

24. A method according to claim 23, further comprising:
plotting said additional determinations of permeability in log format as a function of location in said borehole.

25. A method according to claim 23, wherein:
said generating additional determinations comprises determining each additional determination substantially according to $$k_i = \frac{1}{8F_i}\rho^2 \frac{T_{2oci}^2 T_{2b}^2}{(T_{2b} - T_{2oci})^2}$$

where $T_{2b}$ is a bulk transverse relaxation of water, and i is an index of said plurality of locations such that $k_i$ is the permeability at the i'th of said plurality of locations along said length, $F_i$ is the formation factor at the i'th of said plurality of locations and $T_{2oci}$ is the $T_{2oc}$ at the i'th of said plurality of locations along said length.

26. A method according to claim 25, wherein:
said generating additional determinations comprises generating additional determinations of permeability of a plurality of locations in said earth formation of a same or similar lithology along a portion of said borehole other than said length as a function of said measurements of said NMR tool corresponding to each of said plurality of locations along said portion and as a function of said surface relaxivity.

27. A method according to claim 18, wherein:
said drawdown tool is a single probe tool.

28. A method according to claim 27, wherein:
said computing a surface relaxivity comprises computing substantially according to $$k_{e\omega}^0 = \frac{1}{8F_\omega}\rho^2 \frac{T_{2\omega oc}^2 T_{2b}^2}{(T_{2b} - T_{2\omega oc})^2},$$

where $\rho$ is said surface relaxivity, $k_{e\omega}^0$ is said permeability determination of said single probe tool, $T_{2b}$ is a measure of bulk transverse relaxation of water, $F_w$ is a formation factor of said formation at said location, and $T_{2woc}$ is an observed critical spin—spin relaxation time of a water occupied pore.

29. A method according to claim 28, wherein:
said $T_{2woc}$ for said location is found substantially according to $$p_{cw} = \frac{\int_{T_{2\omega oc}}^{T_{2oc}} T_{2o}^{-\nu} (T_{2b} - T_{2o})^\nu g_{\omega o}(T_{2o}) dT_{2o}}{\int_0^{T_{2oc}} T_{2oc}^{-\nu} (T_{2b} - T_{2o})^\nu g_{\omega o}(T_{2o}) dT_{2o}}$$

where $p_{cw}$ is a critical percolation probability for water occupied pores, $T_{2o}$ is an observed spin—spin decay made by the NMR tool, $T_{2b}$ is a measure of bulk transverse relaxation of water, $T_{2woc}$ is a critical observed spin—spin relaxation time for water occupied pores, $g_{wo}$ is a probability density function for water occupied pores, and $\nu$ is a geometric factor related to the formation at said location.

30. A method according to claim 29, wherein:
said generating a determination of permeability of a location comprises generating said determination substantially according to $$k = \frac{1}{8F}\rho^2 \frac{T_{2oc}^2 T_{2b}^2}{(T_{2b} - T_{2oc})^2}$$

where k is said determination of permeability, $T_{2oc}$ is a critical observed spin—spin relaxation time, and F is the formation factor.

31. A method according to claim 30, further comprising:
generating additional determinations of permeability of a plurality of locations in said earth formation of a same or similar lithology to said location as a function of said measurements of said NMR tool corresponding to each of said plurality of locations and as a function of said surface relaxivity.

32. A method according to claim 31, further comprising:
plotting said additional determinations of permeability in log format as a function of location in said borehole.

33. A method according to claim 31, wherein:
said generating additional determinations comprises determining each additional determination substantially according to $$k_i = \frac{1}{8F_i}\rho^2 \frac{T_{2oci}^2 T_{2b}^2}{(T_{2b} - T_{2oci})^2}$$

where $T_{2b}$ is a bulk transverse relaxation of water, and i is an index of said plurality of locations such that $k_i$ is the permeability at the i'th of said plurality of locations, $F_i$ is the formation factor at the i'th of said plurality of locations and $T_{2oci}$ is the $T_{2oc}$ at the i'th of said plurality of locations.

34. A method according to claim 27, wherein:
said computing a surface relaxivity comprises, for said location and each location of similar lithology for which a drawdown tool permeability determination has been made, calculating respective surface relaxivities substantially according to $$k_{e\omega_{Di}}^0 = \frac{1}{8F_{\omega Di}}\rho_{Di}^2 \frac{T_{2\omega oc_{Di}}^2 T_{2b}^2}{(T_{2b} - T_{2\omega oc_{Di}})^2}$$

where Di is a depth index for said location and said each location of similar lithology, and determining said surface relaxivity ρ as an average of said respective surface relaxivities.

35. A method according to claim 34, wherein:
said generating a determination of permeability of a location comprises generating said determination substantially according to $$k = \frac{1}{8F}\rho^2 \frac{T_{2oc}^2 T_{2b}^2}{(T_{2b} - T_{2oc})^2}$$

where k is said determination of permeability, and F is the formation factor.

36. A method according to claim 35, further comprising:
generating additional determinations of permeability of a plurality of locations in said earth formation of a same or similar lithology to said location as a function of said measurements of said NMR tool corresponding to each of said plurality of locations and as a function of said surface relaxivity.

37. A method according to claim 36, further comprising:
plotting said additional determinations of permeability in log format as a function of location in said borehole.

38. A method of investigating an earth formation traversed by a borehole by utilizing a nuclear magnetic resonance (NMR) tool, said method comprising:
using measurements obtained from the NMR tool which has been in the borehole, finding a critical observed spin—spin relaxation time ($T_{2oc}$) or a function thereof for a location in said formation; and
computing a determination of permeability of said location in said earth formation using said $T_{2oc}$ or said function thereof.

39. A method according to claim 38, wherein:
said computing comprises using a determination of surface relaxivity of said formation at said location or at a location of similar lithology.

40. A method according to claim 39, wherein:
said determination of surface relaxivity is obtained by finding a critical observed spin—spin relaxation time ($T_{2oc}$) or a function thereof for said location and using said $T_{2oc}$ or said function thereof in computing said surface relaxivity.

41. A method according to claim 40, wherein:
said determination of surface relaxivity is obtained by utilizing a permeability determination of a drawdown tool which investigated said location or a location of similar lithology in the formation.

42. A method according to claim 41, further comprising:
generating additional determinations of permeability of a plurality of locations in said earth formation of a same or similar lithology to said location as a function of said measurements of said NMR tool corresponding to each of said plurality of locations and as a function of said surface relaxivity.

43. A method according to claim 42, further comprising:
plotting said additional determinations of permeability in log format as a function of location in said borehole.

44. A method according to claim 42, wherein:
said generating additional determinations comprises determining each additional determination substantially according to $$k_i = \frac{1}{8F_i}\rho^2 \frac{T_{2oci}^2 T_{2b}^2}{(T_{2b} - T_{2oci})^2}$$

where ρ is said surface relaxivity, $T_{2b}$ is a bulk transverse relaxation of water, and i is an index of said plurality of locations such that $k_i$ is the permeability at the i'th of said plurality of locations, $F_i$ is the formation factor at the i'th of said plurality of locations and $T_{2oci}$ is the $T_{2oc}$ at the i'th of said plurality of locations.

45. A method according to claim 38, wherein:
said function of $T_{2oc}$ is $T_{2ic}$, an intrinsic critical T2.

* * * * *